United States Patent [19]
Norton

[11] Patent Number: 5,989,180
[45] Date of Patent: Nov. 23, 1999

[54] REMOVABLE EXTERNAL CLOSURE DEVICE FOR MANAGING FEMALE URINARY INCONTINENCE

[75] Inventor: William J. Norton, Lawrenceville, Ga.

[73] Assignee: C.R. Bard, Inc., Murray Hill, N.J.

[21] Appl. No.: 09/058,948

[22] Filed: Apr. 10, 1998

Related U.S. Application Data

[60] Provisional application No. 60/043,571, Apr. 11, 1997.

[51] Int. Cl.$^6$ ........................................ A41F 2/00
[52] U.S. Cl. ............................................ 600/29
[58] Field of Search ................ 600/29–32, 573, 600/574; 128/885, 887

[56] References Cited

U.S. PATENT DOCUMENTS

| | | | |
|---|---|---|---|
| 5,755,236 | 5/1998 | Dann et al. | 128/885 |
| 5,813,973 | 9/1998 | Gloth | 600/29 |
| 5,885,204 | 3/1999 | Vergano | 600/29 |
| 5,895,349 | 4/1999 | Tihon | 600/29 |
| 5,908,379 | 6/1999 | Schaefer et al. | 600/29 |

FOREIGN PATENT DOCUMENTS

| 96/39989 | 12/1996 | WIPO | 600/29 |
|---|---|---|---|

*Primary Examiner*—Samuel Gilbert
*Attorney, Agent, or Firm*—Jones & Askew, LLP

[57] ABSTRACT

A removable external closure device is disclosed for managing female urinary incontinence. The device includes a resilient, deformable, hollow body portion and a flange which seals against the tissue surrounding the urethral orifice. When the body portion is squeezed and the flange positioned against the tissue surrounding the urethral orifice, the resilience of the body portion creates a vacuum which holds the device in place and closes the urethral orifice. The device is configured to promote tearing of the flange after a predetermined period of normal use so as to insure that the patient will change the device regularly and thus minimize the possibility of creating an infection or tissue irritation that could result from use of a contaminated or dirty device. In one aspect of the invention tearing is promoted by at least the flange being formed of a composition which exhibits a low tear strength. In another aspect of the invention tearing is promoted by an interruption, such as a short radial slit, in the periphery of the flange.

23 Claims, 2 Drawing Sheets

REMOVABLE EXTERNAL CLOSURE DEVICE FOR MANAGING FEMALE URINARY INCONTINENCE

CROSS-REFERENCE TO RELATED APPLICATION

This application claims priority of U.S. Provisional Application Ser. No. 60/043,571, filed Apr. 11, 1997.

TECHNICAL FIELD

The present invention relates generally to a device for controlling female urinary incontinence. More specifically the invention relates to a removable external closure for the human female urethra.

BACKGROUND OF THE INVENTION

Female urinary incontinence is a widespread problem affecting millions of adult females worldwide. A wide variety of treatments have been proposed, ranging from surgical procedures to various devices which restrict or close the urethra. While the devices are less invasive than surgical procedures, they suffer their own disadvantages. Many of the proposed devices include components which reside within the urethra or the vagina. These devices can be uncomfortable to the patient when inserted or applied. They are often inconvenient and unsanitary to use. Further they can be a source of irritation and possible infection to the patient.

Thus there is a need for an improved device for managing female urinary incontinence which minimizes or eliminates discomfort to the patient when applied.

There is also a need for an improved device for managing female urinary incontinence which is convenient and sanitary to use.

There is a further need for an improved device for managing female urinary incontinence which is comfortable to wear and which minimizes the potential for infection.

SUMMARY OF THE INVENTION

Stated generally, the present invention comprises an improved closure device for managing female urinary incontinence. The device is convenient in that it is worn externally and is removable. The device minimizes or eliminates discomfort to the patient when applied and worn. The device is sanitary to use and minimizes the potential for infection resulting from wearing a contaminated or dirty device.

Stated somewhat more specifically, the present invention comprises a removable external closure device for managing female urinary incontinence. The device has a resilient and at least partially deformable body portion open at its lower end and defining a chamber therewithin. A peripheral flange is located at the lower end of the body portion. The flange has a tissue-contacting surface and is sufficiently flexible to seal against the skin of a patient. The body portion and the flange are configured such that when the body portion is compressed and the tissue-contacting surface of the flange is positioned against the tissue surrounding the urethral orifice of a human female patient, the resilience of the body portion exerts a vacuum against the seal formed by the flange against the tissue which holds the closure device in place and closes the urethral orifice to attain continence.

In a first aspect, at least the flange of the closure device is formed from a composition which has a tear strength of less than fifty pounds per inch, preferably less than twenty pounds per inch. This low resistance to tear In a second aspect, the closure device comprises means for creating a location of weakness to promote tearing of the flange after a predetermined period of use. According to one embodiment the means for creating a location of weakness comprises a flange which is tapered in cross-section to an extremely thin portion adjacent the periphery. According to a second embodiment the means for creating a location of weakness comprises an interruption in the periphery of the flange, such as a radially inwardly extending slit.

Thus it is an object of the present invention to provide an improved device for managing female urinary incontinence.

It is another object of the present invention to provide an improved closure device for managing female urinary incontinence which minimizes or eliminates discomfort to the patient when applied and worn.

A further object of the present invention is to provide an improved device for managing female urinary incontinence which is convenient and sanitary to use.

Still another object of the present invention is to provide an improved device for managing female urinary incontinence which minimizes the potential for infection.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
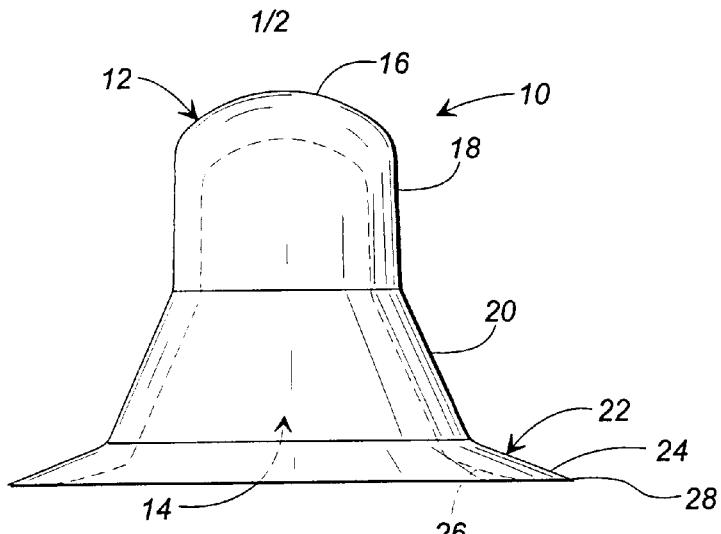
FIG. 1 is a side view of a female urinary incontinence device according to the present invention.
Figure 2:
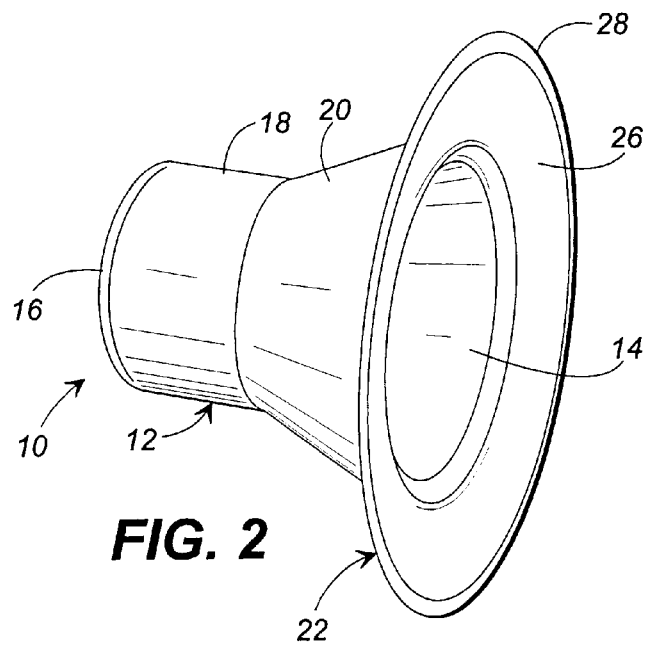
FIG. 2 is a perspective view of the device of FIG. 1.
Figure 3:
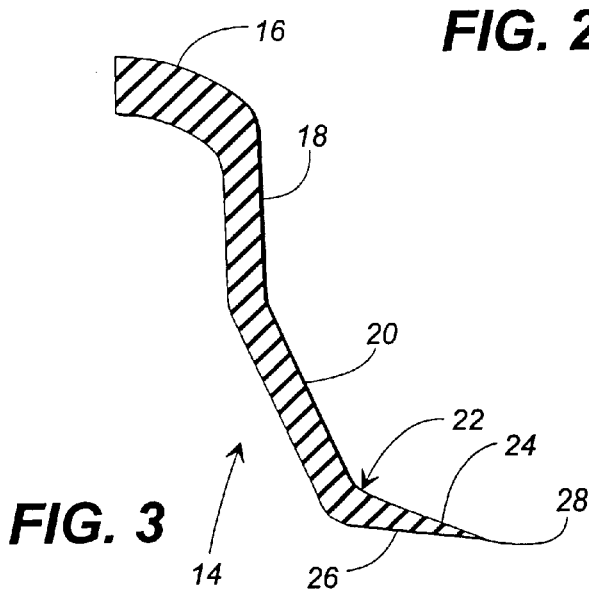
FIG. 3 is an enlarged cross sectional view of a portion of the wall of the device of FIG. 1.

Referring now in more detail to the drawings, in which like numerals indicate like elements throughout the several views, FIGS. 1–3 illustrate a device 10 for managing female urinary incontinence. The device 10 includes a bell-shaped body portion 12 defining a hollow interior 14. The device 10 has a convex upper end 6. The body portion 12 has a generally cylindrical upper body portion 18 extending downward from the periphery of the upper end 16. The upper body portion 18 flares outward at its lower end into a frustoconical lower body portion 20. At the lower end 22 of the lower body portion 20 an annular flange 24 tapers outward and slightly downward. The lower surface 26 of the flange 24 comprises a body-contacting surface.

As can perhaps best be seen in FIG. 3, the flange 24 tapers to a feathered edge adjacent the rim 28. With this design, the edge section is extremely malleable and demonstrates very little resistance to taking a shape. Therefore, it will fit most females and result in very little force against the tissue, while still forming a seal against the tissue capable of maintaining a vacuum.

In the disclosed embodiment, the width of the device 10 at its upper end is slightly over 0.5 inches in diameter. The width of the device at its lower end is approximately 1.375 inches in diameter. The device is slightly under an inch in height.

Figure 4:
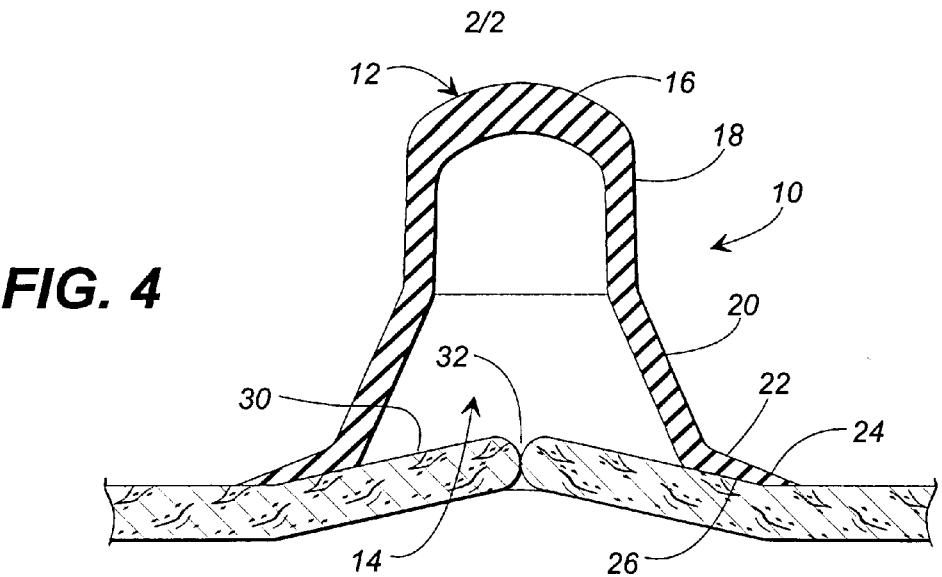
FIG. 4 is a cross sectional view showing the use of the device of FIG. 1 to close the female urethra.

FIG. 4 shows the urinary incontinence device 10 in use. The body portion 12 of the device 10 is squeezed by the patient to partially collapse the side walls, and the flange 24 is brought into contact with the tissue 30 surrounding the meatus urinarius or urethral orifice 32. When the patient releases the compressive force, the resilience of the compound from which the device 10 is manufactured causes the body portion 12 to attempt to return to its normal, uncompressed configuration. As the body portion 12 attempts to return to its normal configuration, the seal of the flange 24 against the tissue 30 surrounding urethral orifice 32 creates a vacuum which holds the device 10 in place. This vacuum creates a gentle compression of the area surrounding the urethral orifice 32 and thus forms a closure which externally closes the urethral orifice to urine flow.

The device 10 is formed using a conventional injection molding process. A novel aspect of the present invention is a unique silicone rubber compound from which the device 10 is formed. Pure silicone rubber exhibits a very low resistance to tear. Accordingly, before silicone rubber can be used in most medical applications, it becomes necessary to add a suitable filler, such as a fumed silica filler, to increase the tear resistance of the compound. Conventional silicone rubber compounds used in medical applications exhibit a tear strength of approximately 125 lbs./inch.

In the compound of the disclosed device, the fumed silica filler has been mostly removed to make what is essentially a purified silicone rubber. Reducing the fumed silica filler also eliminates a source of irritation to the patient and thus makes the device 10 more tissue friendly. In addition, a low molecular weight silicone oligomer, that is, a plasticizer, is added in an amount less than 10% by weight to further reduce the tear strength of the composition. When the fumed silica filler is reduced, however, the modulus of elasticity of the composition is reduced. Since elasticity is crucial to the functioning of the device, it is necessary to compensate for the reduction in the modulus of elasticity resulting from reducing the amount of fumed silica filler. In the disclosed embodiment, a hydrogen-containing polydimethyl siloxane is added to raise the modulus of elasticity of the compound. More specifically, the molar ratio of active hydrogen groups to reactive vinyl groups on the base polydimethyl siloxane is increased to increase the modulus of elasticity of the compound.

The resulting silicone rubber compound of the present invention has the following characteristics:

| | |
|---|---|
| Tensile Strength: | 200–600 lbs/in$^2$ |
| Elongation: | 100–500% |
| Modulus of elasticity at 25% strain: | 1–20 lbs/in$^2$ |
| Modulus of elasticity at 50% strain: | 20–50 lbs/in$^2$ |
| Modulus of elasticity at 100% strain: | 50–150 lbs/in$^2$ |
| Tear strength: | 5–50 lbs/in |

As can be seen, with less filler in the compound, the resultant tear property of the device 10 is very low. In the preferred embodiment, sufficient silica filler is removed from the silicone rubber to create a silicone rubber compound having a tear strength of between 5 and 50 lbs./inch, and preferably between 5 and 20 lbs./inch. With the low tear property and the very thin flange 24, the device 10 will physically tear after a period of normal use. The resultant product 10 thus becomes a disposable device with a very limited life, namely, one to two weeks of normal use. This feature insures that the patient will change the device regularly and minimize the possibility of creating an infection or tissue irritation that could result from use of a contaminated or dirty device.

Figure 5:
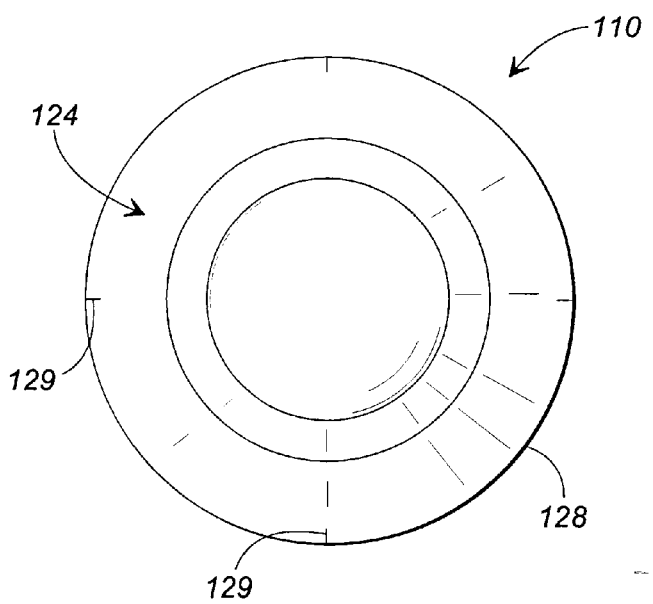
FIG. 5 is a top view of an alternate embodiment of a female urinary incontinence device according to the present invention.
Figure 6:
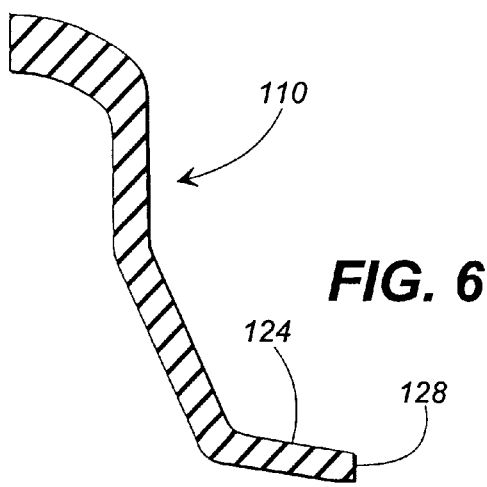
FIG. 6 is an enlarged cross sectional view of a portion of the wall of the device of FIG. 5.

It will be appreciated that the extremely thin feathered edge of the first embodiment serves as a means to create a location of weakness which promotes tearing of the soft material after a predetermined period of use. FIGS. 5 and 6 illustrate a second embodiment 110 of the female urinary incontinence device which comprises a different means for creating a location of weakness. The device 110 is identical to the device 10 except for the flange 124 at the lower end of the device. Unlike the flange 24 of the device 10, the flange 124 of the device 110 is not tapered but instead maintains a fairly constant thickness from its inner edge to its outer edge 128 (FIG. 6). To form a region of weakness to promote tearing, radial slits 129 are formed in the flange 124. The slits 129 begin at the outer periphery 128 of the flange 124 and extend radially inward. It has been found that a slit 129 of approximately 0.050 inches is a sufficient interruption in the periphery of the flange 124 to promote tearing, while being sufficiently minute as not to draw the attention of the user, who might mistake the slits for defects in the closure device. After a period of one to two weeks of normal use, the low tear strength of the compound will cause tears to begin at the slits 129 and propagate outward, rendering the device 110 unusable.

While the slits 129 have been found to be particularly effective in providing a region of weakness to promote tearing, it will be appreciated that other forms of interruptions in the periphery of the flange 124 can also serve this purpose, including notches, scallops, and the like. Also, while the use of a thin flange 24 and interruptions in the flange 124 have been disclosed as constituting separate means for creating zones of weakness to promote tearing, it will be understood that these concepts can be used in combination, e.g., a thin flange and slits in combination.

Also, while the embodiments disclosed above are formed entirely from a single low-tear-strength compound, similar results can be obtained by forming the flange 24, 124 from a compound exhibiting low resistance to tear and forming the body portion 12 from a different composition. This approach would make it possible to focus on the resilience and elasticity of the compound from which the body portion is formed, while maintaining the advantage of low tear strength in the region of the flange 24, 124.

Finally, it will be understood that the preferred embodiment has been disclosed by way of example, and that other modifications may occur to those skilled in the art without departing from the scope and spirit of the appended claims.

What is claimed is:

1. A removable external closure device for managing female urinary incontinence, comprising:

a resilient and at least partially deformable body portion open at a lower end and defining a chamber therewithin; and a peripheral flange at the lower end of said body portion, said flange having a tissue-contacting surface and being sufficiently flexible to seal against the skin of a patient;

said body portion and said flange being configured such that when said body portion is compressed and said tissue-contacting surface of said flange is positioned against the tissue surrounding the urethral orifice of a human female patient, the resilience of said body portion exerts a vacuum against the seal formed by said flange against said tissue which holds said closure device in place and closes the urethral orifice to attain continence;

at least said flange being formed from a composition which has a tear strength of less than fifty pounds per inch.

2. The closure device of claim 1, wherein said flange is formed from a composition which has a tear strength of from five to fifty pounds per inch.

3. The closure device of claim 1, wherein said flange is formed from a composition which has a tear strength of less than twenty pounds per inch.

4. The closure device of claim 1, wherein said flange is formed from a composition which has a tear strength of from five to twenty pounds per inch.

5. The closure device of claim 1, wherein said flange further comprises means for creating a location of weakness to promote tearing of said flange after a predetermined period of use.

6. The closure device of claim 5, wherein said flange comprises a periphery, and wherein said means for creating a location of weakness comprises said flange being tapered in cross-section such that an area adjacent the periphery of said flange is thinner than an area spaced apart from the periphery of said flange.

7. The closure device of claim 5, wherein said flange comprises a periphery, and wherein said means for creating a location of weakness comprises an interruption in the periphery of said flange.

8. The closure device of claim 7, wherein said interruption in the periphery of said flange comprises a slit formed in the periphery of said flange.

9. The closure device of claim 8, wherein said slit extends radially inward from said periphery of said flange.

10. The closure device of claim 9, further comprising slits extending radially inward from a plurality of locations around said periphery.

11. A removable external closure device for managing female urinary incontinence, comprising:

a resilient and at least partially deformable body portion open at a lower end and defining a chamber therewithin; and a peripheral flange at the lower end of said body portion, said flange being comprised of a material having a tear strength, said flange having a configuration, and said flange having a tissue-contacting surface and being sufficiently flexible to seal against the skin of a patient;

said body portion and said flange being configured such that when said body portion is compressed and said tissue-contacting surface of said flange is positioned against the tissue surrounding the urethral orifice of a human female patient, the resilience of said body portion exerts a vacuum against the seal formed by said flange against said tissue which holds said closure device in place and closes the urethral orifice to attain continence;

said configuration of said flange and said tear strength of said material being selected to promote tearing of said flange after a predetermined period of use not to exceed two weeks.

12. The closure device of claim 11, wherein said flange comprises a periphery, and wherein said configuration of said flange comprises said flange being tapered in cross-section such that an area adjacent the periphery of said flange is thinner than an area spaced apart from the periphery of said flange such that said thinner area of said flange adjacent said periphery, in combination with said tear strength of said material, promotes tearing of said flange after said predetermined period of use not to exceed two weeks.

13. The closure device of claim 11, wherein said material of said flange has a tear strength of from five to fifty pounds per inch.

14. The closure device of claim 11, wherein said material of said flange has a tear strength of less than twenty pounds per inch.

15. The closure device of claim 11, wherein said material of said flange has a tear strength of from five to twenty pounds per inch.

16. A removable external closure device for managing female urinary incontinence, comprising:

a resilient and at least partially deformable body portion open at a lower end and defining a chamber therewithin; and a peripheral flange at the lower end of said body portion, said flange having a tissue-contacting surface and being sufficiently flexible to seal against the skin of a patient;

said body portion and said flange being configured such that when said body portion is compressed and said tissue-contacting surface of said flange is positioned against the tissue surrounding the urethral orifice of a human female patient, the resilience of said body portion exerts a vacuum against the seal formed by said flange against said tissue which holds said closure device in place and closes the urethral orifice to attain continence;

said flange further comprising a periphery, said periphery of said flange having an interruption therein to promote tearing of said flange after a predetermined period of use.

17. The closure device of claim 16, wherein said interruption in the periphery of said flange comprises a slit formed in the periphery of said flange.

18. The closure device of claim 17, wherein said slit extends radially inward from said periphery of said flange.

19. The closure device of claim 18, further comprising slits extending radially inward from a plurality of locations around said periphery.

20. The closure device of claim 16, wherein said flange is formed from a composition which has a tear strength of from five to fifty pounds per inch.

21. The closure device of claim 16, wherein said flange is formed from a composition which has a tear strength of less than twenty pounds per inch.

22. The closure device of claim 16, wherein said flange is formed from a composition which has a tear strength of from five to twenty pounds per inch.

23. The closure device of claim 16, wherein said predetermined period of use does not exceed two weeks.

* * * * *